United States Patent [19]

Lin et al.

[11] Patent Number: 5,348,872
[45] Date of Patent: Sep. 20, 1994

[54] METHOD FOR ISOLATING MUTANT CELLS

[75] Inventors: Edmund Lin, Boston; Bryan L. Ray, Burlington, both of Mass.

[73] Assignee: President and Fellows of Harvard College, Cambridge, Mass.

[21] Appl. No.: 991,115

[22] Filed: Dec. 16, 1992

Related U.S. Application Data

[63] Continuation-in-part of Ser. No. 856,876, Mar. 24, 1992, abandoned, which is a continuation of Ser. No. 541,895, Jun. 21, 1990, abandoned.

[51] Int. Cl.$^5$ ............... C12N 15/00; C12N 5/00; C12N 1/12; C12N 1/14
[52] U.S. Cl. ............ 435/172.1; 435/69.1; 435/172.3; 435/240.2; 435/252.1; 435/252.2; 435/252.3; 435/252.31; 435/252.33; 435/252.5; 435/254.1
[58] Field of Search ............ 435/69.1, 240.2, 172.1, 435/252, 252.1, 252.2, 252.3, 252.31, 252.33, 252.5, 255, 254, 320.1, 172.2, 172.3

[56] References Cited

U.S. PATENT DOCUMENTS 3,580,810  5/1971  Shiio et al.
4,421,819  12/1983  Breuker.

OTHER PUBLICATIONS

Kavanagh (ed.) (1963) *Analytical Microbiology*, vol. II, Academic Press, N.Y.
Baich et al. (1965) *Biochim. Biophys. Acta* 104:397–404.
Elkind et al. (1967) *The Rabiobiology of Cultured Mammalian Cells*, Gordon and Breach, publishers, pp. 551–552.
Miller (ed.) (1972) *Experiments in Molecular Genetics*, Cold Spring Harbor, Cold Spring Harbor, New York.
Pai (1972) *J. Bacteriol.* 112:1280–1287.
Lawrence et al. (1974) *J. Bacteriol.* 118:41–45.
Kempe et al. (1976) *Cell* 9:541–550.
Grull et al. (1979) *J. Bacteriol.* 137:480–489.
Green (1980) *Second Chem. Congree N. Am. Continent* ISBN 0-8412-0583-3, San Francisco, Abstract No. 16.
Vincenzotto et al. (1982) *Arch. Internat. de Chemi.* 90:B88.
Yamada et al. (1982) *Agric. Biol. Chem.* 46:47–55.
Thompson et al. (1983) *Meth. Enzymol.* 58:308–322.
Yamada et al. (1983) *Agric. Biol. Chem.* 47:1011–1016.
Young et al. (1983) *Science* 222:778–782.
Santhaguru et al. (1985) *Israel J. Med. Sci.* 21:185.
Hibberd (1988) *Iowa St. J. Res.* 62:479–486.
McCusker et al. (1988) *Genetics* 119:303–315.
*Catalogue of Bacterial and Bacteriophages*, (7th ed., 1989).
Hall et al. (1989) *J. Bacteriol.* 143:981–988.
LiMuti et al. (1989) *J. Microbiol. Meth.* 9:129–137.
Chattopadhyay et al. (1991) *J. Gen. Microbiol.* 137:685–691.
Kornberg et al. (1991) *DNA Replication* (2d. ed.) W. H. Freeman, N.Y. p. 172.
*Catalogue of Cell Lines and Hybridomas*, (7th Ed.) American Type Culture Collection, 1992.
Hirt et al. (1992) *Gene* 111:199–206.

*Primary Examiner*—Robert J. Hill, Jr.
*Assistant Examiner*—Gian P. Wang
*Attorney, Agent, or Firm*—Lappin & Kusmer

[57] ABSTRACT

Disclosed is a method for isolating a mutant cell that secretes a desired compound at a level greater than that secreted by a starter cell from which the mutant cell is derived. The method includes contacting a plurality of auxotrophic feeder cells and auxotrophic starter cells together in the solid growth medium. The starter cells produce the desired compound required by the feeder cells and the feeder cells produce a metabolite required by the starter cells. These cells are cultured to produce a plurality of primary colonies, the largest of which include at least one of the mutant cells which overproduces the desired compound.

15 Claims, 1 Drawing Sheet

METHOD FOR ISOLATING MUTANT CELLS

CROSS-REFERENCE TO RELATED APPLICATIONS

The subject matter of this application is a continuation-in-part of copending application Ser. No. 856,876, entitled "Method of Isolating Mutant Cells," filed Mar. 24, 1992, now abandoned, which is a continuation of application Ser. No. 541,895, entitled "Method of Isolating Mutant Cells," filed Jun. 21, 1990, now abandoned.

BACKGROUND OF THE INVENTION

This invention relates to methods of isolating a mutant cell containing one or more mutations which enhance production, excretion or secretion, of a desired compound from the cell compared to a cell without such mutations.

It is common to isolate mutant cells which overproduce a specific metabolite by selecting cells which are resistant to analogs of the metabolite. For example, Yamada et al. (*Agric. Biol. Chem.* (1983) 47:1011). describe the isolation of mutants which overproduce biotin by selecting for cells resistant to a biotin analog. Yamada et al. (*Agric. Biol. Chem.* (1982) 46:47), and Chattopadhyay, et al. (*J. Gen. Microbiol.* (1991) 137:685), isolated methionine-overproducing mutants by selecting cells resistant to ethionine. Hibberd (*Iowa State J. Res.* (1988) 62:479), isolated valine-overproducing mutants, selecting valine resistance). Kempe et al. (*Cell* (1976) 9:541), isolated pyrimidine nucleotide biosynthetic enzyme overproducers, selecting resistance to N-phosphonoacetyl-1-aspartate). Hall et al. (*J. Bacter.* (1989) 143:981), isolated amino acid overproducers in cyanobacteria by selecting antimetabolite analog resistance. In Hall et al. (id.) wild type *Bacillus subtilis* cells were used as a test lawn for screening obvious regulatory mutants from among collections of analog resistant strains. Auxotrophic strains of *B. subtilis* were convenient indicator strains for identification of mutants in Cyanobacteria through observation of syntrophic growth responses. Green (2d Chem. Congress N. Am. Continent, San Francisco, Aug. 22, 1989, Abst. No. 16) describes production of mutant corn cells resistant to lysine- and threonine-induced growth inhibition. Grull et al. (*J. Bacter.* (1979) 137:480,) describe isolation of amino acid overproducing mutants of *E. coli* obtained by mutagenesis and penicillin enrichment. Vincenzotto et al. 90 (*Arch. Internat. de Chemi* (1982) 90:B88) describe isolation of mutants of an alga by mutagenesis and screening on agar medium containing various dyes. Santhaguru et al. (*Israel J. Med. Sci.* (1985) 21:185,) describe use of levulinate, a competitive inhibitor of the heme biosynthetic pathway, for isolation of heme overproducing Rhizobium mutants.

Isolation of cells that make a desired product from a population of cells that do not make the desired product is a problem when the production of the desired compound does not endow the cell with any selective advantage. In these instances, one must develop a method of screening for production of the desired product. A screening method which employs a detector strain present in an overlay was utilized by Pai (*J. Bacteriol.* (1972) 112:1280) to isolate a strain that overproduces biotin. In this method, wild type *E. coli* were mutagenized and plated with an *E. coli* biotin auxotroph. The mutagenized *E. coli* was not itself an auxotroph, and thus, a mutual two-way symbiotic relationship was not achieved. A similar method has more recently been employed to obtain lysine excretors (LiMuti et al. (1989) *Microbiol. Meth.* 9:129). A variation of the overlay method has been developed where a micropore membrane is used to separate the strain from the substrate (U.S. Pat. No. 4,421,849). A problem with these strategies is the limitation on the number of cells that can be screened at one time. The limit is based on the need to distinguish individual colonies on a plate which places the limit, e.g. for bacteria, at 1,000 to 10,000 per each 100 mm diameter plate. If the event resulting in production of the desired compound occurs at a frequency of $10^{-7}$, then 1,000 plates would have to be screened to obtain one event.

SUMMARY OF THE INVENTION

This invention concerns a method for symbiotic amplification of desired mutant cells by using two genetically different populations of cells which cross-feed each other. This invention also includes a method for isolating a mutant cell that secretes a desired compound at a level greater than that secreted by a starter cell from which the mutant cell is derived.

According to one embodiment of the invention, a plurality of the feeder cells and the starter cells are contacted together in or on the surface of the solid growth medium to allow the feeder cells to produce the metabolite and the starter cells to produce the desired compound. These cells are then cultured so that they will grow, divide, and produce a plurality of primary colonies, the largest of which include at least one of the mutant cells.

The term "mutant cell" is meant to encompass any cell which contains one or more mutations which affect the secretion of the desired compound, compared to the starting cell from which the mutant cell is derived. By "derived" it is merely meant that the mutant cell results from growth and cell division of the starting cell and includes one or more mutations compared to the starter cell.

The starter cell is an auxotroph that has a requirement for a metabolite for its survival or division in a solid growth medium. It secretes a desired compound into the solid growth medium and mutates to lack the requirement at a frequency of less than $10^{-10}$ per cell division. In addition, the starter cell has a rate of mutation at least $10^{-6}$ per nucleotide base per cell division, the rate resulting from the presence of a mutator gene or mutation resulting from mutagenesis in the DNA of the starter cell. In some embodiments, the starter cell has a selectable phenotype allowing its ready isolation from the feeder cell.

The feeder cell is also an auxotroph that requires the desired compound for its survival or division in the solid growth medium. It secretes the metabolite required by the starter cell into solid growth medium. In some embodiments, the feeder cell has a selectable phenotype allowing its ready isolation from the starter cell.

The starter and feeder cells may belong to the same or different taxonomical kingdoms, divisions, orders, families, genera, or species. In one preferred aspect of the invention, the starter cell and the feeder cells are cells selected from the group consisting of bacteria, yeast, fungi, animal, plant cell, and human cells. In other embodiments the starter and/or the feeder cells have been genetically engineered or mutagenized to become auxotrophic.

Preferably, the desired compound made by the starter cell and overproduced by the resulting mutant cells is a nutrient, growth factor, enzyme, vitamin, amino acids, cytokine, interleukin, trophic factor, nucleic acid component, cofactor, fatty acid, lipid, polysaccharide, glycolipid, glycoprotein, lipopolysaccharide, or lipoprotein. In some embodiments of the invention, the desired compound is the vitamin such as biotin or any number of amino acids.

The metabolite produced by the feeder cells is meant to include any compound which will allow growth of a starter cell and which is produced during metabolism by another cell. Such metabolite must be excreted into the medium surrounding the cell which produces it either by the cell's secretory mechanism, or other excretory mechanisms. In one embodiment, the metabolite is a nutrient, growth factor, enzyme, vitamin, amino acids, cytokine, interleukin, trophic factor, nucleic acid component, cofactor, fatty acid, lipid, glycolipid, glycoprotein, polysaccharide, lipopolysaccharide, lipoprotein, or fatty acid. In yet another embodiment, the metabolite secreted into the growth medium by the feeder cells may also be a signalling compound which activates a metabolite in the growth medium which is required by the starter cells, or which stimulates the production of the metabolite by another source such as a third cell type. In still another embodiment, the desired compound is a factor which activates or stimulates the production of a metabolite required by the feeder cell.

In another aspect of the invention, the method further includes the additional step of contacting the colony cells with the feeder cells in or on the surface of the solid growth medium, thereby allowing the feeder cells to produce the desired compound and the colony cells to produce the metabolite, and the feeder cells and colony cells to grow, divide, and produce a plurality of secondary colonies. These secondary colonies contain the mutant cell which produces the desired compound.

Other features and advantages of this invention will be apparent from the following description of the preferred embodiments thereof, and from the claims.

BRIEF DESCRIPTION OF THE DRAWINGS

The foregoing and other objects of the present invention, the various features thereof, as well as the invention itself may be more fully understood from the following description, when read together with the accompanying drawings in which.

DESCRIPTION OF THE PREFERRED EMBODIMENT

A new method has been developed for the isolation of mutant cells which overproduce a desired compound. This same method can be used to screen for the excretion of desired compounds that are either produced naturally or are a product of genetic engineering or mutagenesis. The procedure results in the isolation of a single mutant excreting cell from a large population of nonexcreting starter cells.

Figure 1:
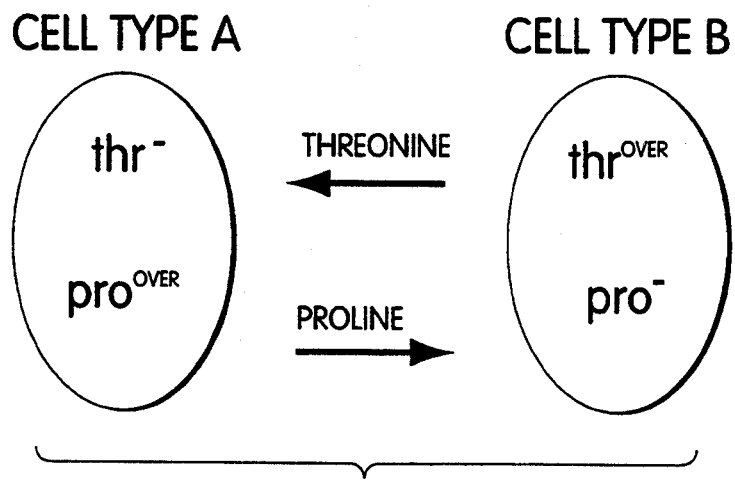
FIG. 1 is a diagrammatic representation of the symbiotic amplification method of the invention.

The basis of this method, and the feature that distinguishes it from all other screening methods currently employed, is the establishment of symbiotic relationship between two cell types dependent on excretion of the desired compound. One embodiment of the method of the invention is depicted in FIG. 1. As shown, Cell type A produces a metabolite that Cell type B requires for growth. However, Cell type A cannot grow unless it is supplied with the desired compound. Cell type B cannot grow unless it is supplied with a metabolite produced by Cell type A. Hence, a two-way symbiotic relationship is established between Cell type A and Cell type B, resulting in the growth of a colony including both cell types directly or indirectly dependent on the excretion of the desired compound.

If Cell type A or B does not normally excrete the metabolite or desired compound, respectively, the cell can be mutagenized to induce excretion or genetically altered to endow the strain with the ability to excrete the metabolite or compound. Both of these methods will lead to a mixed population of Cell type B that does not excrete the desired compound and altered Cell type B (hereinafter referred to as mutant Cell type B*) that does excrete the desired compound. When this mixed population is mixed with Cell type A and immobilized on or in the solid medium, only cells of Cell type A that are near Cell type B, will grow, hence allowing Cell type B, to grow as well. The result is the formation of a mixed primary colony consisting of Cell types A and B*. These cell types can be separated based on their antibiotic or other resistance resulting in the isolation of a pure Cell type B* capable of excreting the desired compound.

The method further includes steps of isolating those primary colonies which include mutant cells (generally the largest colonies growing on a solid medium) and again contacting those cells with further feeder cells to allow further secondary colonies to form. This process may be repeated as many times as desired until a desired mutant cell which copiously excretes the desired compound is isolated.

By a "colony" is meant a group of cells including both starter and feeder cells which manifest themselves on the solid growth medium in a manner detectable by one of ordinary skill in the art. Generally, such colonies will be visible to a naked eye, having a size of greater than 0.1 mm.

If the cell density in the initial screening is high, as is the case if a rare mutation is looked for, the resulting colony will be a mixture of Cell types A, B, and B*. A further round of symbiotic screening using a lower initial cell density will then be needed to isolate a pure population of mutant Cell type B* from resulting secondary colonies.

Starter cells which require metabolites generally have one or more mutations within their DNA which limit or prevent the ability of that starting cell to produce that metabolite. Preferably, the starter cell includes deletions at one or more regions of DNA responsible for production of that metabolite. Such deletions prevent the starting cell from mutating to lack the requirement of the metabolite. If the DNA is not deleted, that cell must contain two, or preferably more, mutations which prevent production of the metabolite, and do not mutate to produce a cell with an ability to produce a metabolite (i.e., revert) at a frequency of greater than $10^{-10}$ per cell division. Since the mutation rate at any particular nucleotide is between $10^{-3}$ and $10^{-10}$ it is preferable that starter cells contain at least 3 mutations within any gene encoding enzymes for the synthesis of the metabolite.

Mutator genes are well known to those of ordinary skill in the art. Generally, they are mutations in a DNA polymerase which causes that polymerase to incorporate nucleotide bases incorrectly. Such incorrect incorporation results in a mutation. Generally, such mutator genes can increase the mutation rate of a cell by between 1,000- and 100,000-fold. The mutation rate of any particular cell can be readily measured by one of ordinary skill in the art, for example, by providing a plasmid comprising the lacZ gene of *E. coli* and measuring the rate of mutation of nucleotide bases within the lacZ gene. It is preferred that the rate of mutation be at least $10^{-6}$ per nucleotide base, preferably at least $10^{-4}$ per nucleotide base, in order to allow rapid mutation of DNA of the starting cells. Because of the presence of such mutator genes within the starter cell, and as discussed above, it is preferable that the genes encoding the metabolite be deleted so that the chance of reversion is practically zero. If other genes mutate to replace the lost function, those genes could either be deleted, mutated or modified to remove the interference.

In another example of the same method, Cell A is a starter cell from which mutants which secrete a desired compound "X" may be isolated. Cell A includes a mutator gene and another gene which genetically blocks the ability of Cell A to grow on glucose. Cell A thus requires a metabolite for growth other than glucose, e.g., acetate or succinate. These compounds must be provided by the feeder cell, Cell B. The mutator gene, for example, mutD, increases the frequency of spontaneous mutation up to about $10^5$ (Kornberg et al. (1991) *DNA Replication* (2d ed). W. H. Freeman, New York p. 172). Also included in Cell A is a gene conferring resistance to streptomycin (rpsL); this resistance allows ready purification of Cell A, and its descendants from Cell B (which is sensitive to streptomycin) by growth in a medium containing streptomycin.

Cell B, the feeder cell, is blocked for the synthesis of the desired compound X. For example, compound X may be a vitamin such as biotin. The starter Cell A secretes this vitamin during growth on acetate and succinate. The feeder cell is deleted for genes requires for utilization of lactose (Δlac) which allows selection against growth of Cell B, even without the use of antibiotic streptomycin. The cell population is simply grown on a medium employing lactose as a carbon source for cell growth. Starter Cell A can grow on this medium; feeder Cell B cannot grow on this medium. Such medium may also contain streptomycin to ensure growth of starter Cell A in favor of feeder Cell B.

When mutations occur in the starter cell which increase production and secretion of a compound required for growth of the feeder cell, the faster the surrounding feeder cells will grow. The faster such feeder cells produce a compound required for growth of the starter cells or mutant cell the faster the starter cell will grow.

The desired compound can be any compound which affects the survival and division of the feeder cell. Generally, such desired compounds are chosen from cellular building blocks, e.g., lipids, fatty acids, vitamins, amino acids, nucleic acid components, cytokines, cofactors, and growth factors such as fibroblast growth factor, an interleukin such as interleukin-1 or -2, or any other equivalent compound.

The desired compound also includes all products that are able to convert, either directly or indirectly, a nonessential compound present in the growth media into an essential compound of the symbiosis. This definition includes all enzymes that are capable of producing, directly or indirectly, an essential nutrient from existing or added non-essential components of the growth media.

Figure 2:
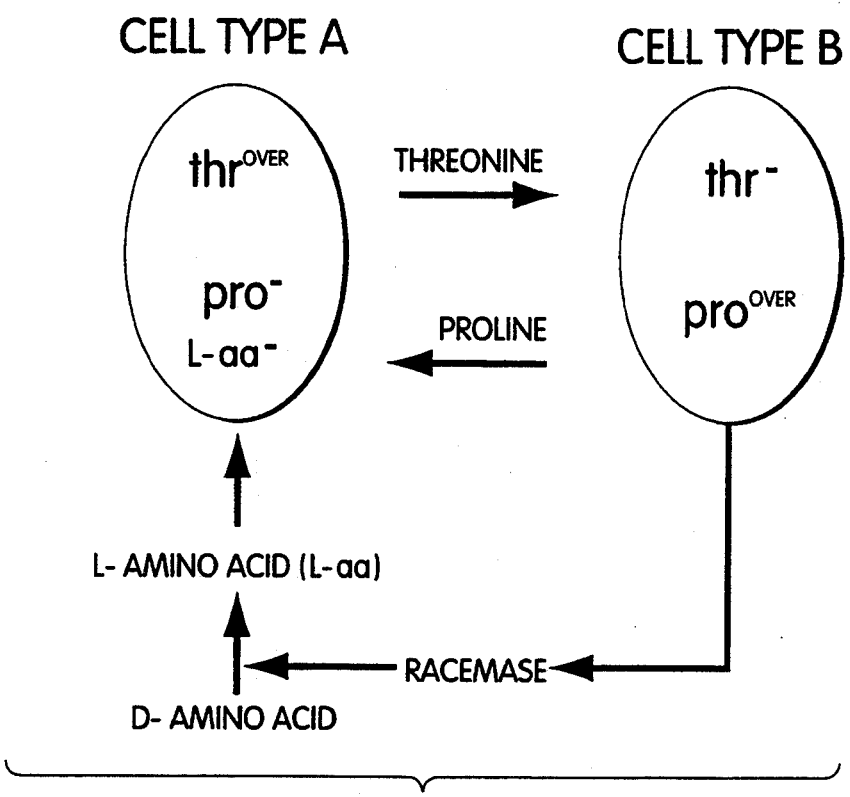
FIG. 2 is a diagrammatic representation of another embodiment of the symbiotic amplification method of the invention.

An example of such an enzymatic product is depicted in FIG. 2. In this example, an *E. coli* strain secretes a racemase. Racemase acts on the D-amino acid, converting it to the L-isomer which is required for growth by Strain A. Formation of the L-amino acid establishes the symbiosis between Strain A and Strain B.

The starter or feeder cell may include mutations which provide a selectable phenotype, for example, resistance to an antibiotic or inability of that cell to grow on a carbon source on which the other cell may grow. The selectable phenotypes allow later separation of the starter and feeder cells from one another, and allow isolation of a starting cell which has mutated to form a mutant cell. The starter and/or feeder cell may include DNA which has been inserted into those cells by recombinant DNA technology, for example, the starter cell may include heterologous genes (i.e., genes from another organism) for the production of the desired compound.

Generally, the feeder cell is able to survive or divide very slowly for only a very limited number of times in the absence of the desired compound. For example, a bacterial feeder cell may have a rate of cell division of less than one cell division in three hours at 37° C. in growth medium lacking the desired compound but otherwise having all required compounds. This compares to a rate of cell division of 1 in 30 minutes when the feeder cell is provided with the desired compound. The rate of cell division of plant and animal cells, or of cells grown under less optimum conditions, may be much lower. It is important in the invention that the feeder cell have a greatly reduced rate of cell division in the absence of the desired compound compared to its rate of cell division in the presence of the desired compound. Thus, in the presence of the desired compound its rate of cell division is enhanced (e.g., at least three-fold and most preferably at least ten-fold); production of the metabolite required by the starter cell is also enhanced in the presence of the desired compound.

Similarly, the starter cell requirement for the metabolite produced by the feeder cell need not be absolute. The absence of such metabolite need only significantly reduce the rate of cell survival or division (i.e., by at least three-fold, preferably ten-fold). More importantly the starter cell must produce only a limited amount of the desired compound in the absence of the metabolite. Thus, both the starter cell and the feeder cell will grow, survive, and divide only poorly in the absence of the other of the starter or feeder cell or in the absence of the metabolite or desired compound. That is, both the starter cell and the feeder cell are dependent upon each other for growth and have a mutual, two-way symbiotic growth relationship.

The appearance of "false positives" or colonies appearing as a result of something other than that which is desired, is avoided because both parental strains have auxotrophies that revert at a rate at least 100-fold less than the number of cells to be plated. For example, because between $10^7$ and $10^8$ *E. coli* cells will be plated, auxotrophic reversion rates of less than $10^{-9}$ and $10^{-10}$ are desired. To assure that reversion does not interfere, it is best to have deletion or insertion mutations in the genes responsible for the auxotrophies.

Thus, the invention provides a method for simple selection of desired mutant cells. There is no need to provide agents which cause mutations in the starter cells, nor a need for tedious screening of mutated cells to determine whether they contain a desired phenotype. The method automatically selects mutant cells which have the property of secreting desired compounds. These mutant cells can be readily isolated after selection in the method of this invention, and used in standard procedures for production of the desired compound.

In order to determine whether any particular cell pair is suitable for use in the symbiotic amplification method, the two types of cells are simply inoculated onto a solid medium lacking the desired compound but including the metabolite which allows growth of Cell A; for example, the medium lacks biotin but includes acetate. The starter cells are able to grow on this medium to form a patch of cells, or a streak, on the plate. The feeder Cell B is unable to grow on this plate unless the starter cells secrete some biotin. Growth of the Cell B adjacent the streak of Cell A demonstrates that the cells may act symbiotically with respect to biotin secretion.

The types of cells that can be employed in such a screening includes all unicellular organisms and eucaryotic cells that can be cultured. If two different organisms or cell types are employed, the requirements are that a growth medium be used that is capable of supporting the growth of both organisms or cell types.

To determine appropriate cell pairings the growth requirements of each individual cell type can be compared. For example, The American Type Culture Collection publishes the *Catalogue of Bacteria and Bacteriophages*, (7th ed., 1989) which lists hundreds of compounds that are produced or required by numerous genera. This list can be used to define a pair of strains in which one strain produces something the other strain requires for growth. One of the strains can then be altered through techniques known in the art to require a desired compound for growth. For example, mutagenesis can be carried out using conventional mutagens such as N-methyl-N'-nitro-N-nitrosoguanidine, ethyl methanesulfonate, and ultraviolet irradiation (see, e.g., Miller (Ed.) (1972) *Experiments In Molecular Genetics*, Cold Spring Harbor, N.Y.). Strain B can then be mutagenized using similar techniques. A screening for the desired compound can then be set up. If there is no selectable drug resistance to distinguish the strains, they can be separated based on auxotrophic requirements. Listings of other cultured prokaryotic and eucaryotic cells are available to prepare other pairings. (See, e.g., *Catalogue of Cell Lines and Hybridomas* (7th Ed.) American Type Culture Collection, 1992).

It is important to ensure that the physical diffusion of metabolites and the desired compound in the growth medium is proportionate to the rate of consumption of that metabolite by surrounding cells requiring such compounds. The relative rates of these two processes can be changed so as not to allow excessive concentration of the desired compound in the medium. This can be accomplished by altering the incubation temperature, which has little effect on physical diffusion of a metabolite, but has a significant effect on the growth rate of a cell and thus the consumption of the metabolite by that cell. An optimal temperature can be determined by standard procedure. Alternatively, enzymes or antibodies that inactivate the desired compound may be added to the medium. Finally, analogs that compete with the desired compound may be added to the medium.

Also of importance is that the optimal cell density and ratio of starter cells to feeder cells be established. This can be done by standard procedure. For example, by altering the ratio of those cells until the desired results are obtained.

The colonies may be grown within or on a surface of the solid growth medium, e.g., agar. In addition, the percentage of agar to liquid within the medium can be altered to reduce the rate of spread of growing cells. Again, optimal conditions for any pair of cells can be readily determined by standard procedure.

When first starting the cross-feeder selection procedure described above it may be necessary to provide a small amount of the required metabolite and/or desired compound in order to allow some initial growth of the cells. Such initial growth should be limited to a few cell divisions, sufficient to allow a symbiotic relationship to start.

Using the screening procedure described herein, $10^7$ cells can be screened on a single 100 mm plate. In addition, the method is adaptable to a wide range of products. The method is amenable to screening enzymatic activities and does not require the use of radioactive or colorimetric substrates.

Furthermore, the method of the invention enables the engineering of new biosynthetic pathways by recombinant DNA technology, for example, by cloning a gene or set of genes into a plasmid or chromosome and transforming an appropriate cell with that plasmid. This method also can be used to improve such engineered pathways. Since different species of microbial cells, and even plant or animal cells, can be used in this method, the method can be used to create mutant cells which produce almost any desired compound. Such cells can be genetically altered to allow selection of mutants that secrete a compound which is not a normal cellular component of that cell. Thus, for example, cells can be engineered to produce a growth factor, such as fibroblast growth factor (FGF) and overproducing mutants selected by growing those starter cells which secrete FGF in the presence of feeder cells which require FGF for growth or cell division. Such feeder cells may include a natural receptor for the FGF, or may naturally required FGF for cell growth. The starter cell may have a requirement for a carbon source other than glucose, as described above, or any other analogous requirement well known to those of ordinary skill in the art.

The invention allows isolation and selection of desired mutant cells without use of a large number of growth dishes. A large number of starter cells can be introduced onto one plate with feeder cells and growth of only one mutant cell-containing colony from such starter cells readily detected.

The method can also be used to isolate symbiotic mixtures of two cells both of which are mutated but still depend on one another for growth.

It is also possible to use this method for concurrent selection of several mutant cells at once. For example, when three or more cells are used, each of which depends on one of the other cells for growth, mutants in each of these cells may be selected. Specifically, if three cells, A, B, and C, are used and A requires a factor from C, B requires a factor from A, and C requires a factor from B, mutant cells of A and B, or A and C, or B and C can be simultaneously selected. One such cell, e.g., Cell A, may even be chosen so that it is able to supply Cell B or Cell C with a required factor for growth.

The following examples illustrate the preferred mode of making and practicing the present invention, but are not meant to limit the scope of the invention since alternative methods may be utilized to obtain similar results.

EXAMPLE 1

Feasibility Studies with Auxotrophic E. coli Mutants

CR46 is an E. coli strain having a proB$^c$, thr43::Tn10 genotype resulting in the overproduction of proline and a non-revertible threonine requirement. E. coli Strain B overproduces threonine and has a non-revertible proline requirement. Its genotype is unknown. After 24 hours of growth at 37° C., approximately 1,000 colonies were visible. Approximately $10^7$ CR46 E. coli cells (Strain A in FIG. 1) were plated with $10^8$ E. coli strain B cells on solid media lacking proline and threonine.

This experiment demonstrates that the method of the invention is feasible.

Then, E. coli strain CR46 is plated with E. coli strain CR47. CR47 has a mutD5::Tn10, proC::Tn5 genotype resulting in a mutator phenotype with a non-revertible proline requirement. CR46 is then modified, by methods known in the art, so as to require for growth the compound of interest that is overproduce by mutant CR46. CR46 and CR47 then are grown overnight at 37° C. in minimal media containing the appropriate supplements and antibiotics. The cells are then washed once in minimal media lacking supplements. Approximately $10^7$ CR47 cells are mixed with $10^8$ CR46 cells, and plated on medium lacking proline and threonine. Colonies appearing after 48 hours are serially diluted and replated on the medium with $10^8$ cells of CR46. Colonies appearing on this second round of screening are streaked onto LB+kanamycin plates to isolate the CR47 mutant which overproduces the compound of interest. CR47 is kanamycin-resistant due to the present of Tn5.

EXAMPLE 2

Bacterial Studies with Genetically Altered Strain

E. coli Strain CR65 cells (Strain A of FIG. 2) overproduces threonine and has a non-revertible proline requirement. This strain CR65 is altered either by mutagenesis or genetic engineering so as to require the product of a particular enzyme for growth. E. coli Strain B has a proB$^c$, thr43::Tn10 genotype, resulting in proline overproduction and a non-revertible threonine requirement. Strain B is either mutagenized or genetically engineered to express the desired enzyme. It is required that either the enzyme substrate and product be freely permeable to the outer membrane of the bacterial strains involved, or that the enzyme be secreted into the media or that it is expressed on the outer surface of the outer membrane of strain B. Approximately $10^8$ CR65 cells are plated with $10^7$ strain B cells on growth medium lacking proline and threonine. Colonies appearing after 48 hours are serially diluted and replated on the same medium with $10^8$ CR65 cells. Colonies appearing after this second round of screening are then streaked onto growth plates containing tetracycline to isolate the strain B cells producing the desired enzyme.

EXAMPLE 3

Mammalian Cell Studies

Murine macrophages, when stimulated to proliferate by colony-stimulating factor (CSF), produce interleukin-1 (IL-1). IL-1 stimulates murine fibroblasts to proliferate. Therefore, by cloning into the murine fibroblast cell line a symbiosis can be established between a macrophage and fibroblast. These cells are obtainable from the gene encoding CSF.

Vectors have been developed for cloning DNA in mouse fibroblasts (Hirt et al. (1992) Gene 111:199-206. In these systems, expression of the cloned gene is induced by glucocorticoids such as dexamethasone. A cDNA library from lymphocytes cloned into the fibroblast expression vector is used as the source of putative CSF. The cDNA library is cloned into the fibroblasts.

Transformed fibroblasts and macrophages are grown separately in Dulbecco's modified Eagle's medium supplemented with appropriate growth factors. Cells are washed, and $10^6$ transformed fibroblasts are plated with $10^6$ macrophages on the media lacking CSF and IL-1, but containing dexamethasone. Colonies appearing are picked, diluted, and plated with $10^6$ macrophages on the same medium. Colonies which appear are picked and plated on Dulbecco's modified Eagle's medium supplemented for the growth of fibroblasts. Individual colonies are then assayed for CSF production.

EXAMPLE 4

Plant and Yeast Studies

Methods for growing the tobacco plant, N. tabacum, in cell culture are available to those knowledgeable in the art. N. tabacum requires nicotinic acid for growth. S. cerevisiae available from the American Type Culture Collection (ATCC) accession no. (9763), which produces nicotinic acid, is mated with S. cerevisiae ATCC accession no. 9896, which requires biotin for growth. Progeny that produce nicotinic acid and require biotin for growth are designated S. cerevisiae*. Cultured cells from the tobacco plant N. tabacum are mutagenized using conventional methods for plant mutagenesis; the resultant population is designated N. tabacum*.

Both types of cells are grown up in minimal media supplemented with the necessary nutrients. The media required for maintaining N. tabacum in cell culture also supports the growth of the yeast, S. cerevisiae. Cells are washed with minimal media. $10^7$ S. cerevisiae* cells are mixed with $10^6$ cells N. tabacum* and plated on minimal media without nicotinic acid and biotin. When colonies appear, they are picked, diluted, mixed with $10^7$ cells of S. cerevisiae* and plated. Colonies appearing are treated with fungicide to kill the S. cerevisiae,* cells. The remaining tobacco cells are assayed for biotin production using conventional biotin screening methods.

EXAMPLE 5

Genetically Engineered Bacteria and Mutagenized Yeast Studies

E. coli strain P48 (Pai (1972) J. Bacteriol. 112:1280-1287) which excretes biotin, is transduced with the P1 phage prepared from E. coli strain Y1088 (Young et al. (1983) Science 222:778-789). Kanamycin-resistant transductants (hereafter referred to as E. coli*) require proline for growth. S. cerevisiae strain ATCC accession no. 9896 requires biotin for growth. Spontaneous canavanine-resistant isolates of ATCC accession no. 9896 and are designated S. cerevisiae*.

S. cerevisiae is mutagenized to obtain putative proline overproducers using conventional methods (e.g. McCusker et al. (1988) *Genetics* 119:303–315). Then the E. coli, and mutagenized S. cerevisiae* cells are each grown overnight in a minimal broth supplemented with the appropriate amino acids to support growth. After overnight growth, both cultures are pelleted by centrifugation, and the cells washed once in minimal media without proline or biotin.

Approximately $10^7$ mutagenized S. cerevisiae* are mixed with $10^8$ E. coli, and the mixture plated on minimal agar plates lacking proline and biotin. E. coli and S. cerevisiae have similar growth requirements, hence standard minimal media used for the growth of S. cerevisiae will suffice. After 48 hours, colonies that appear are picked, serially diluted, mixed with $10^8$ E. coli*, and replated on the medium. After 24 to 48 hours, colonies that appear are picked and streaked onto minimal media plates containing canavanine which will not permit E. coli* to grow. The degree of proline overproduction is then assessed using conventional methods (see, e.g., Kavanagh (ed.) *Analytical Microbiology*, Vol II, (1963) Academic Press, New York).

EXAMPLE 6

Genetically Engineered E. coli and Mutagenized B. flavum

E. coli strain CR41, which excretes proline, is transduced with the P1 phage prepared from an E. coli strain containing the lysA::Tn10 genotype using conventional methods (Miller (ed.) (1972) *Experiments in Molecular Genetics*, Cold Spring Harbor Laboratory, CSH, N.Y.). Tetracycline-resistant transductants (hereafter referred to as E. coli*) require lysine for growth. B. flavum* (ATCC accession no. 31838) is mutagenized using conventional methods for E. coli Miller (ed.) (1972) *Experiments in Molecular Genetics*, Cold Spring Harbor Laboratory, CSH, N.Y. to obtain a mutant (hereafter referred to as B. flavum*) that requires proline for growth.

E. coli* and mutagenized B. flavum* are each grown overnight in a minimal broth supplemented with the appropriate amino acids to support growth. After overnight growth, both cultures are pelleted by centrifugation and the cells washed once in minimal media without proline or lysine. Approximately $10^7$ mutagenized B. flavum* are mixed with $10^8$ E. coli* and the mixture plated on minimal agar plates lacking proline and lysine. Because E. coli and B. flavum have similar growth requirements, standard minimal media used for the growth of B. flavum will suffice. After 48 hours, colonies that appear are picked, serially diluted, mixed with $10^8$ E. coli*, and replated on the medium. After 24–48 hours, colonies that appear are picked and streaked onto Brain Heart Infusion media with streptomycin which does not permit E. coli* to grow. The degree of lysine overproduction is assessed using conventional methods (see, e.g., Kavanagh (ed.) *Analy. Microbiol.* (1963) Vol. II, Academic Press, New York).

EXAMPLE 7

E. coli, Mutant Studies

An E. coli strain carrying the mutant ubiC allele, ubiC 437, requires 4-hydroxybenzoate for growth on succinate as the sole carbon source. This strain produces biotin as does wild-type E. coli. It is designated Strain A. E. coli Strain B requires biotin for growth and carries a mutD5::Tn10 genotype which was introduced via P1 transduction.

Strains A and B are grown overnight at 37° C. in succinate minimal media supplemented with the necessary nutrients. Cells from both cultures are washed once in succinate minimal media without supplements and suspended in the same media. Approximately $10^8$ cells of Strain A are mixed with $10^7$ cells of Strain B and the mixture is plated on succinate minimal solid media lacking 4-hydroxybenzoate and biotin. Colonies appearing after 48 hours are picked, serially diluted in succinate minimal media without supplements, mixed with $10^8$ cells of Strain A, and plated on solid media as before. Colonies appearing after 48 hours are streaked for single cells on LB-tetracyline plates, and individual colonies are assayed for 4-hydroxybenzoate production (see, e.g., Lawrence et al. (1974) *J. Bacteriol.* 118:41–45).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A method for isolating a mutant cell that secretes a desired compound at a level greater than that secreted by a starter cell from which said mutant cell is derived, said method comprising the steps of:

(a) providing a starter cell selected from the group consisting of bacterial, fungi, and animal cells, which:

(i) is an auxotroph that has a requirement for a metabolite for survival or division of the starter cell in a solid growth medium, the metabolite being selected from the group consisting of nutrients, amino acids, growth factors, cofactors, interleukins, vitamins, and carbohydrates, the metabolite being other than the desired compound;

(ii) mutating to lack the requirement at a frequency of less than $10^{-10}$ per cell division;

(iii) has a rate of mutation at least $10^{-6}$ per nucleotide base per cell division, the rate resulting from the presence of a mutator gene or mutation resulting from mutagenesis in the DNA of the starter cell; and (iv) secretes the desired compound into the solid growth medium;

(b) providing a feeder cell selected from the group consisting of bacterial, fungi, and animal cells, which:

(i) is an auxotroph that requires the desired compound for its survival or division in the solid growth medium, the desired compound being selected from the group consisting of nutrients, amino acids, growth factors, interleukins, cofactors, vitamins, and carbohydrates, the desired compound being other than the metabolite; and (ii) secretes the metabolite into solid growth medium;

(c) contacting a plurality of the feeder cells and the starter cells together in or on the surface of the solid growth medium to allow the starter cells to produce the desired compound and the feeder cells to produce the metabolite; and (d) culturing the feeder and starter cells to grow, divide, produce a plurality of primary colonies, wherein the primary colonies which are the largest include at least one of the mutant cells.

2. The method of claim 1 wherein the starter cell has a selectable phenotype allowing its ready isolation from the feeder cell.

3. The method of claim 1 wherein the feeder cell has a selectable phenotype allowing its ready isolation from the starter cell.

4. The method of claim 1 wherein the starter cell and the feeder cell belong to different genera.

5. The method of claim 1 wherein said starter cell and the feeder cell are chosen from cells belonging to different species.

6. The method of claim 1 wherein the starter cell or the feeder cell are bacterial cells.

7. The method of claim 1 wherein the starter cell and the feeder cell are bacterial cells.

8. The method of claim 1 wherein the starter cell or the feeder cell are mammalian cells.

9. The method of claim 1 wherein the starter cell and the feeder cell are mammalian cells.

10. The method of claim 1 wherein the starter or feeder cells have been genetically engineered or mutagenized so as to become auxotrophic.

11. The method of claim 1 wherein the starter cell and the feeder cell have been genetically engineered or mutagenized to become auxotrophic.

12. The method of claim 1 wherein said desired compound is a vitamin.

13. The method of claim 12 wherein said vitamin is biotin.

14. The method of claim 1 comprising the additional step of contacting the primary colony cells with the feeder cells in the solid growth medium, thereby allowing the feeder cells to produce the metabolite compound and the colony cells to produce the desired compound, and the feeder cells and colony cells to grow, divide, and produce a plurality of secondary colonies.

15. The method of claim 1 wherein the desired compound secreted into the growth medium by the starter cell is an enzyme which activates or stimulates the production of a metabolite required by the feeder cells.

* * * * *

UNITED STATES PATENT AND TRADEMARK OFFICE
CERTIFICATE OF CORRECTION

PATENT NO. : 5,348,872
DATED : September 20, 1994
INVENTOR(S) : Edmund Lin and Bryan L. Ray It is certified that error appears in the above-indentified patent and that said Letters Patent is hereby corrected as shown below:

Column 1, line 13, before "BACKGROUND OF THE INVENTION", insert the following paragraph:

--The United States Government has rights in this patent pursuant to NIH Grant Nos. GM11983, GM39693, and GM40993.--

Signed and Sealed this

Twenty-seventh Day of December, 1994

Attest:

BRUCE LEHMAN

Attesting Officer     Commissioner of Patents and Trademarks